United States Patent [19]

Mettes

[11] Patent Number: 5,198,094
[45] Date of Patent: Mar. 30, 1993

[54] COUNTERFLOW DEVICE TO REDUCE THE NEGATIVE IMPACT OF CONTAMINATING MATERIALS USED IN MOISTURE SENSITIVE APPARATUSES OR PROCEDURES

[75] Inventor: Jacob Mettes, Doylestown, Pa.

[73] Assignee: Meeco, Incorporated, Warrington, Pa.

[21] Appl. No.: 629,439

[22] Filed: Dec. 18, 1990

[51] Int. Cl.$^5$ ............................................. G01N 27/26
[52] U.S. Cl. ................................ 204/430; 204/153.22; 204/400; 204/409; 73/29.01; 73/29.02
[58] Field of Search ................. 73/29.01, 29.02, 29.04; 204/409, 430, 400, 153.22

[56] References Cited

U.S. PATENT DOCUMENTS

| | | | |
|---|---|---|---|
| 3,050,371 | 8/1962 | Dowson et al. | 204/409 |
| 3,234,117 | 2/1966 | Rost et al. | 204/409 |
| 4,098,650 | 7/1978 | Sayles | 204/153.22 |
| 4,800,000 | 1/1989 | Zatko et al. | 204/409 |

FOREIGN PATENT DOCUMENTS 485373  9/1975  U.S.S.R. .............................. 204/430

OTHER PUBLICATIONS

"Ultraclean Gas Delivery Systems-Part I" by K. Sugiyama and T. Ohmi in Microcontamination, Nov. 1988, pp. 49-54.
"Sub-ppb Analysis of Nitrogen Gas by APINS" by T. Kimura, J. Mettes and H. Schark, presented at Technical Symposium of Semicon East 89 in Boston, Massachusetts, Sep. 1989.

Primary Examiner—T. Tung
Attorney, Agent, or Firm—Ratner & Prestia

[57] ABSTRACT

A counterflow device adapted for an analyzer engaging a gas stream and having a sensor for measuring a component of that stream. Because at least one element disposed between the gas inlet and gas outlet of the sensor typically emits unwanted impurities, the device diverts a portion of the gas stream as a counterflow directed toward the impurity-emitting element or elements. The counterflow enters the outlet without contacting the sensor of the analyzer.

16 Claims, 6 Drawing Sheets

COUNTERFLOW DEVICE TO REDUCE THE NEGATIVE IMPACT OF CONTAMINATING MATERIALS USED IN MOISTURE SENSITIVE APPARATUSES OR PROCEDURES

TECHNICAL FIELD

This invention relates to a device for reducing the negative impact of certain contaminating materials. Such materials may be incorporated in the apparatuses or procedures which use gas and which are sensitive to the moisture contained in that gas. The invention can be applied, for example, to apparatuses and procedures that measure the water concentration in gases. More particularly, the invention concerns a device which detects, within a short response time, concentrations of water as low as a few parts per billion by volume.

BACKGROUND OF THE INVENTION

In many industrial processes, the water concentration of flowing gas streams must be measured and analyzed with a high degree of speed and accuracy. Such measurement and analysis is required because the water concentration is often critical to the quality of the product produced. Consequently, many complex and sophisticated devices are available for measuring water in gases.

These devices typically incorporate an electrolytic cell operating under the principles of Faraday's Law, although other types of hygrometers based on other principles also exist. Basically, an electrolytic cell consists of a hollow glass tube with at least two electrically isolated electrodes (wires) helically wound in parallel around the inside and covered with a hygroscopic film. The electrodes cover approximately half of the surface area of the inside wall of the cell. The gas to be analyzed enters the cell at a known flow rate and the film absorbs all moisture molecules present in the gas flow. A voltage is supplied across the electrodes, which electrolyzes the moisture in the film. The current generated measures the rate at which the moisture molecules are electrolyzed. Once equilibrium is reached, the rate at which moisture molecules enter the cell will exactly match the rate at which such molecules are electrolyzed. Consequently, the water concentration in the gas will be known without any further calibration.

Such devices are generally unable, however, to measure extremely low concentrations of water with a response time sufficiently short to accommodate many applications.

For example, the electrolytic cell described in U.S. Pat. No. 4,800,000 to D. A. Zatko, incorporated herein by reference, is sensitive to water concentrations on the order of about 2,000 to 5 parts per billion by volume. That cell reaches, following a change in the entering moisture concentration, about ninety percent of the final equilibrium value in about five minutes—even for changes as small as 1.5 ppm. Although such levels of sensitivity and response time are impressive, improvement is desirable.

Specifically, the known electrolytic devices use a packing material such as an epoxy filler to mechanically fix the detection cell in place. The epoxy also serves as an electrical insulator for the electrodes and as a leak-tight barrier between the entrance and exit of the actual detector, which is typically the hollow glass tube of the cell. The epoxy barrier assures that the sample gas will flow only through, and not around, the glass tube of the cell. Finally, the epoxy provides a leak-tight barrier where the electrical connections penetrate through the metal housing of the cell body.

As a result of its many functions, the packing material is present in the vicinity of both the inlets and outlets of the detection cell. Such materials are known to be relatively porous and to absorb or emit water from or into the gas stream. It is known that the outgassing, absorption, and desorption properties of packing materials, such as plastics, epoxy, and the like, form an obstacle to reaching low water concentrations in high purity gas systems.

Several possible mechanisms limit the performance of these hygrometers through the presence of such contaminating materials. One such mechanism, outgassing, occurs when residual water contained in the packing material migrates out of the material and eventually joins the flowing gas stream under test. This contamination prevents the instrument from reaching lower detection limits.

A second mechanism limiting the response time is absorption of the moisture present in the gas stream by the packing material and desorption (or emission) from that material into the gas stream. On the one hand, this mechanism allows previously absorbed moisture to desorb back into the gas flow upon a change from wet to dry gas. When the gas under analysis is relatively dry and has been analyzed for a relatively long time, on the other hand, the surface of the packing material may become dry. Consequently, the material may absorb moisture from the gas at the inlet for some time before the moisture present in the gas can reach the actual detector (and enter the glass tube in an electrolytic cell). In both cases, the moisture measurements of the cell will take a long time to reach equilibrium under the changed conditions.

For an electrolytic cell, the negative effects caused by the presence of epoxy at the inlet side of the cell are seen directly. But the presence of epoxy at the outlet side also has adverse effects. Contamination at the outlet side occurs through back diffusion of moisture against the small sample gas flow exiting the glass tube.

In general, the configuration of the prior art devices contributes to the unfavorable mechanisms of outgassing, absorption, and desorption. These mechanisms, in the case of hygrometers, increase the response time and limit detection of very low concentrations. Further, these mechanisms are temperature and pressure dependent.

SUMMARY OF THE INVENTION

Accordingly, one object of the present invention is to provide a device for reducing the negative impact of certain contaminating materials. Such materials may be incorporated in the apparatuses or procedures which use gas and which are sensitive to the moisture contained in that gas. Another object of the present invention is to provide an improved device for the rapid determination of moisture in the gas phase. Another object of this invention is to provide a device with a low detection limit, able to analyze a moisture concentration on the order of 1 part per billion by volume. Another object of the invention is to reduce the response time of hygrometers.

These objects are achieved in the present invention by configuring the main components of the hygrometer in a counterflow arrangement. A counterflow is very effective to control the travel of moisture. It is difficult for moisture molecules to diffuse against a flow of dry gas. Experiments at MEECO, Inc. have shown that, in a 100 cc/minute dry gas flow through a ¼-inch diameter pipe, the impact of a source of moisture of 1600 ng/minute on the moisture concentration two inches upstream was smaller than two parts per billion.

An explanation of this behavior exists in the "sticky" nature of the water molecule. Such molecules propagate through pipelines, for example, by continuously establishing a local absorption/desorption equilibrium with the inner wall of the pipeline. At the normal operating gas pressures of a few atmospheres, the mean free path of the gas molecules (the distance covered by a molecule without making a collision) is extremely small. One molecule makes millions of collisions each second, some of them with the pipe wall. The probability that a water molecule will stick on the wall after a wall collision depends on the number of water molecules already stuck on, or absorbed by, the wall. Thus, the probability that a molecule will stick is high for a dry wall and relatively low for a wet wall. Contrast this behavior of water molecules with "non-sticky" molecules: the probability that the latter will stick is very low and depends little on the number of like molecules already absorbed by the surface of the wall.

For the reasons discussed above, a counterflow arrangement is very effective in controlling the travel of moisture. Such an arrangement also is helpful, however, for detection devices which measure the content of other trace components in a gas flow such as, for example, traces of oxygen in nitrogen. Because, unlike moisture molecules, the gas phase components are not "sticky", these components will migrate from a contamination source to the measurement device against a counterflow better than will the moisture molecules. Nevertheless, contamination of a gas flow by less sticky gas phase components or even by particles can be prevented—especially if a larger counterflow passing through a longer, smaller diameter geometry is provided.

In the present invention the objects and advantages described above are achieved by placing components sensitive to moisture contamination, such as the actual sensor, upstream in the gas flow relative to the possible sources of contamination. Gas that flows away from the sensor is discarded, so contamination of that gas downstream of the components necessary for detection will not adversely impact measurement. "Contamination" includes outgassing of moisture and the similarly unfavorable mechanisms of moisture absorption and desorption. Possible sources of such contamination are, in general, any soft, non-metal materials, porous materials, or materials with a relatively large surface area. "Dead" volumes (those volumes devoid of gas flow) can also contaminate.

Sources of contamination include, as just discussed, areas or points passed by the sample flow before it reaches the analyzer or testing device. Another possible form of contamination by such areas may be illustrated, for example, by the conventional "chilled mirror" hygrometer. In such an instrument, the moisture concentration is measured by observing the onset of condensation of water (having reached its dew point) on the surface of a mirror that is cooled while monitoring the mirror's temperature. The mirror is positioned on top of a cooling device. Certain areas or points on the cooling device which are in direct contact with the sample gas may be cooler than the surface of the mirror cooled by that device. Accordingly, moisture may condense on those areas of the cooling device before it can condense on the mirror—which is the analyzer's actual sensor. In this sense, such areas will be sources of "contamination".

A counterflow of exiting gas directed toward the cooling device and away from the surface of the mirror will prevent premature condensation of moisture in the sample gas stream. In this situation, as soon as gas molecules from the sample gas stream reach the proximity of an area of potential contamination they are drawn into the exiting counterflow. Consequently, such molecules will be removed from the sample gas stream which reaches the sensor. The sample gas stream which reaches the sensor will have avoided contact, therefore, with the contaminating areas.

For an electrolytic cell, specific sources of contamination include the materials used to mechanically position the detector, those materials used to create a leak-tight barrier and force the gas through the cell, and those materials which seal and electrically isolate the electrodes to and from the detector. In an electrolytic cell, the counterflow geometry of the present invention uses the bypass gas flow and the sample gas flow exiting the detection cell to prevent contamination of the measured sample flow. Contaminants must flow against the exiting flows, in such an arrangement, to adversely affect measurement.

In still another aspect of the present invention, the packing material is replaced by a compression-type, glass-metal connection (such as a soft ferrule) combined with a weldable or solderable, electrical, leak tight, ceramic feedthrough for the electrodes. Such a connection and feedthrough are described in co-pending U.S. application Ser. No. 07/592,348 entitled "Epoxy-Less Low-Level Moisture Measurement System and Method" filed on Oct. 3, 1990 by Jacob Mettes. That application is incorporated herein in its entirety. The contamination-reducing counterflow configuration disclosed herein can be applied to a device including such a connection and feedthrough, thereby reducing the impact of possible contamination by the soft material, the ceramic material, and the dead areas.

DESCRIPTION OF THE DRAWINGS

The foregoing and other aspects, features, and advantages of the invention will be apparent from the following description and drawings, in which.

DETAILED DESCRIPTION

Figure 1:
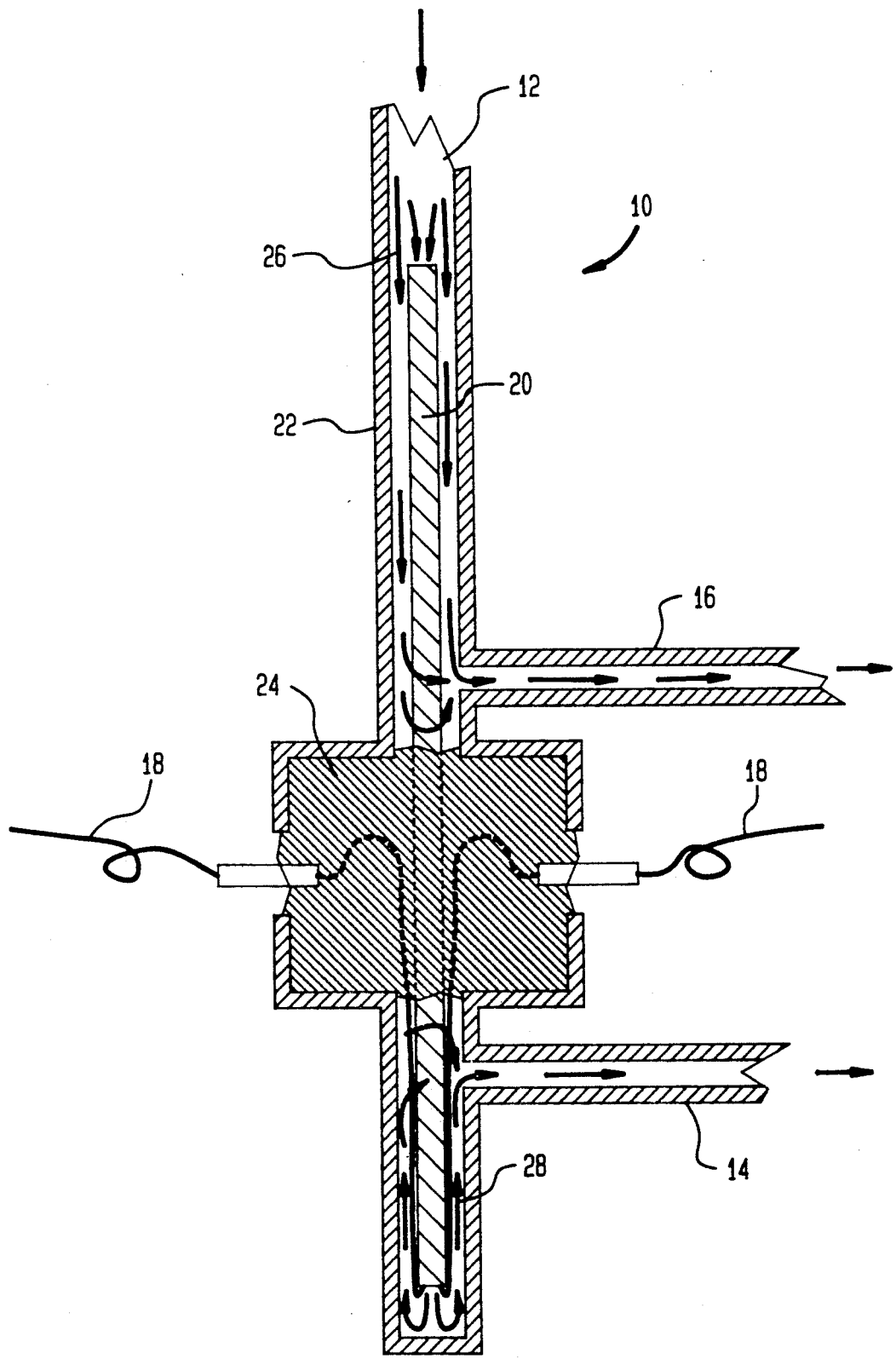
FIG. 1 is a generalized schematic representation of an electrolytic cell incorporating counterflow geometry.

Referring now to FIG. 1, an analyzer or device 10 according to the invention passes a sample gas through hollow electrolytic detection unit or sensor 20 so that the gas contacts a moisture absorbent coating (not shown) on the inside surface of unit 20. The absorbed water is electrolyzed and the water concentration determined by measuring the electrical current used in accordance with Faraday's Law. The result of that determination may be manipulated as desired to produce a suitable output reading, for example, in parts per billion (ppb).

Device 10 generally comprises an inlet 12, an outlet 14, a bypass outlet 16, electrodes 18, and a detection unit 20 in a suitable housing 22. The electrolytic detection unit 20 is typically held in place with epoxy 24 or another packing material which often has less favorable properties towards outgassing and absorption/desorption of water, restricting device 10 to a higher detection limit and a slower response time. In the present invention, the entrance and exit of detection unit 20 are located in the gas stream at a significant distance from the level of the packing material, thereby minimizing the possibility that moisture will migrate from the packing material into either the entrance or exit of the detection unit 20.

The gas flow indicated by arrows 26 is such that any moisture which escapes from the packing material 24 must flow against the current of the gas stream in order to reach the entrance of the detection unit 20. Similarly, the output gas shown by arrows 28 flows toward the packing material before exiting. This counterflow configuration minimizes the possibility that moisture, escaping from the packing material or from any other source such as the sample flow outlet 14, will enter the exit of the detection unit 20. As far as absorption/desorption is concerned, the gas entering unit 20 has not been in contact with the packing material 24, avoiding the slow response time consequent upon such contact.

Figure 2A:
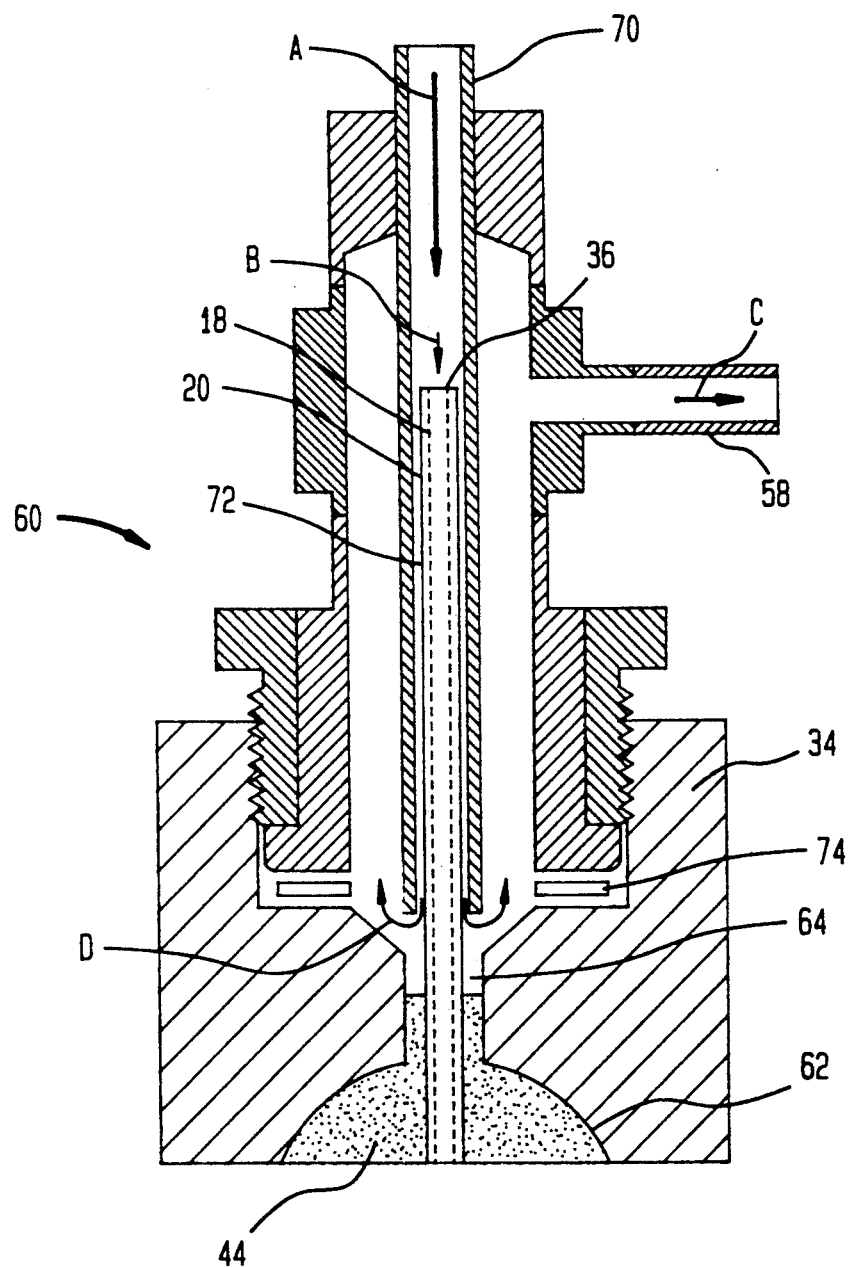
FIG. 2a is a cross-section of an electrolytic cell according to the present invention highlighting one embodiment of the counterflow configuration at the inlet.
Figure 2B:
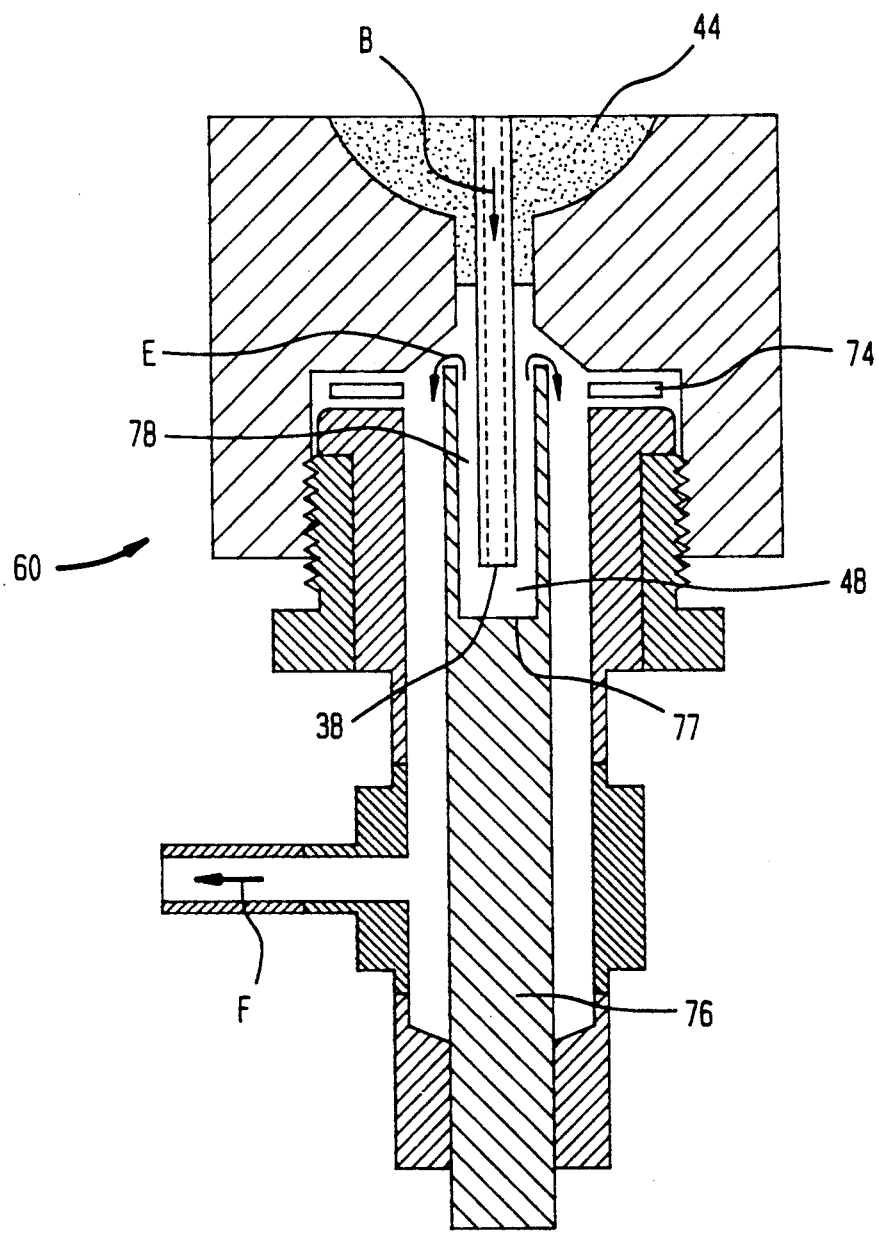
FIG. 2b is a cross-section of an electrolytic cell according to the present invention highlighting the counterflow configuration at the outlet.

Turning to FIGS. 2a and 2b, one embodiment of an electrolytic cell according to the present invention is shown.

A central opening 62 is provided in housing 34 to admit epoxy 44. Opening 62 is formed to pass horizontally more than halfway, but not completely, through housing 34. The size of opening 62 is substantially less than either the height of housing 34 or the length of detection unit 20. Epoxy 44 is admitted to opening 62 during manufacture of cell 60 and partly fills the space 64 between unit 20 and housing 34.

The central admission of epoxy 44 enables epoxy 44 to be substantially confined to the center of housing 34 surrounding the center of unit 20, hence to be substantially isolated from entrance 36 and exit 38 of unit 20. Further, only a very small surface area of epoxy 44 actually contacts the gas, thereby reducing contamination by epoxy 44.

The present invention provides a counterflow geometry which relies upon the flowing gas stream to exclude extraneous moisture or other impurities from entering detection unit 20.

Hollow tubing or sleeve 70, preferably of electropolished stainless steel and having an inner diameter greater than the outer diameter of unit 20, surrounds the upper end of unit 20. The relationship between tubing 70 and unit 20 creates a counterflow (illustrated by arrow D in FIG. 2a), as will now be described.

The gas to be sampled, designated by arrow A in FIG. 2a, first enters tubing 70. As gas A passes down tubing 70, it encounters entrance 36 of unit 20. At entrance 36, gas A separates into sample gas B, which passes into unit 20 and is analyzed, and gas D. Rather than enter unit 20, gas D passes between unit 20 and tubing 70 in cavity 72. At the termination of tubing 70, gas D is forced upward towards the bypass flow exit 58 because gasket 74, housing 34, and epoxy 44 seal alternative openings. Gas D then exits cell 60 as bypass gas C, so called because it is that portion of gas A which did not form sample B but, instead, bypassed unit 20.

Any moisture which might leak from epoxy 44 must travel upward in cavity 72, against the force of gas D, to reach entrance 36 and contaminate sample gas B. As discussed, a counterflow like that of gas D makes such travel difficult, if not impossible; thus, contamination of sample gas B is virtually eliminated.

Figure 3:
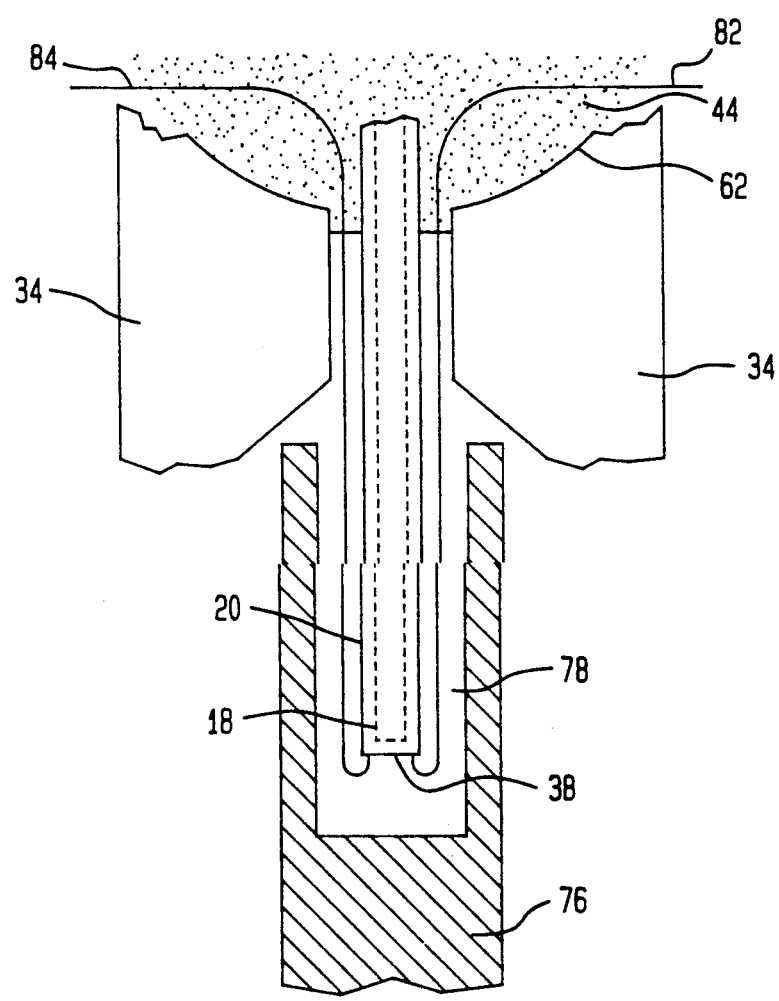
FIG. 3 shows the electrode wires as they exit the outlet of the detection unit when configured as in FIGS. 2a and 2b.

Similarly, the present invention provides a counterflow geometry near exit 38 to prevent contamination of sample gas B. Rod 76 protrudes upward into passage 48. Rod 76 is preferably of electropolished stainless steel and has a cylindrical notch 77 formed in its top. Notch 77 has an inner diameter greater than the outer diameter of unit 20 and leaves sufficient space for the two electrode wires 82, 84 (not shown in FIG. 2b), stretched along the outside of unit 20 (see FIG. 3), to avoid contacting adjacent components. Details about electrode wires 82, 84 will be discussed below with reference to FIG. 3. Moreover, rod 76 extends sufficiently far into passage 48 to enable notch 77 to surround the lower end, including exit 38, of unit 20. The relationship between rod 76 and unit 20 forms a dam, creating a counterflow E, as will now be described.

Following analysis, sample gas B exits unit 20 at exit 38. Thereafter, gas B enters channel 78, formed between unit 20 and the side walls of notch 77, and creates counterflow E. Counterflow E travels up channel 78 and leaves cell 60 as exit gas F.

Clearly, any moisture which might leak from epoxy 44 must travel downward in channel 78, against the stream of counterflow E, to reach exit 38. Then the moisture must diffuse against sample gas flow B in order to be detected. The presence of counterflow E makes such travel difficult, if not impossible; thus, contamination of sample gas B is reduced.

Finally, the difficulties involved in the existing fabrication process can be reduced, according to the present invention, by improving the method of connecting wires 82 and 84 to the electrical components external to cell 60. As show in FIG. 3, electrode wires 82 and 84 are routed directly into central opening 62 to be filled with epoxy 44. After epoxy 44 is poured and sets, it fixes wires 82 and 84 in position. Thus, wires 82 and 84 can be safely connected to the electrical terminals of device 10 without risking forces exerted on those wires as they enter unit 20.

Figure 4:
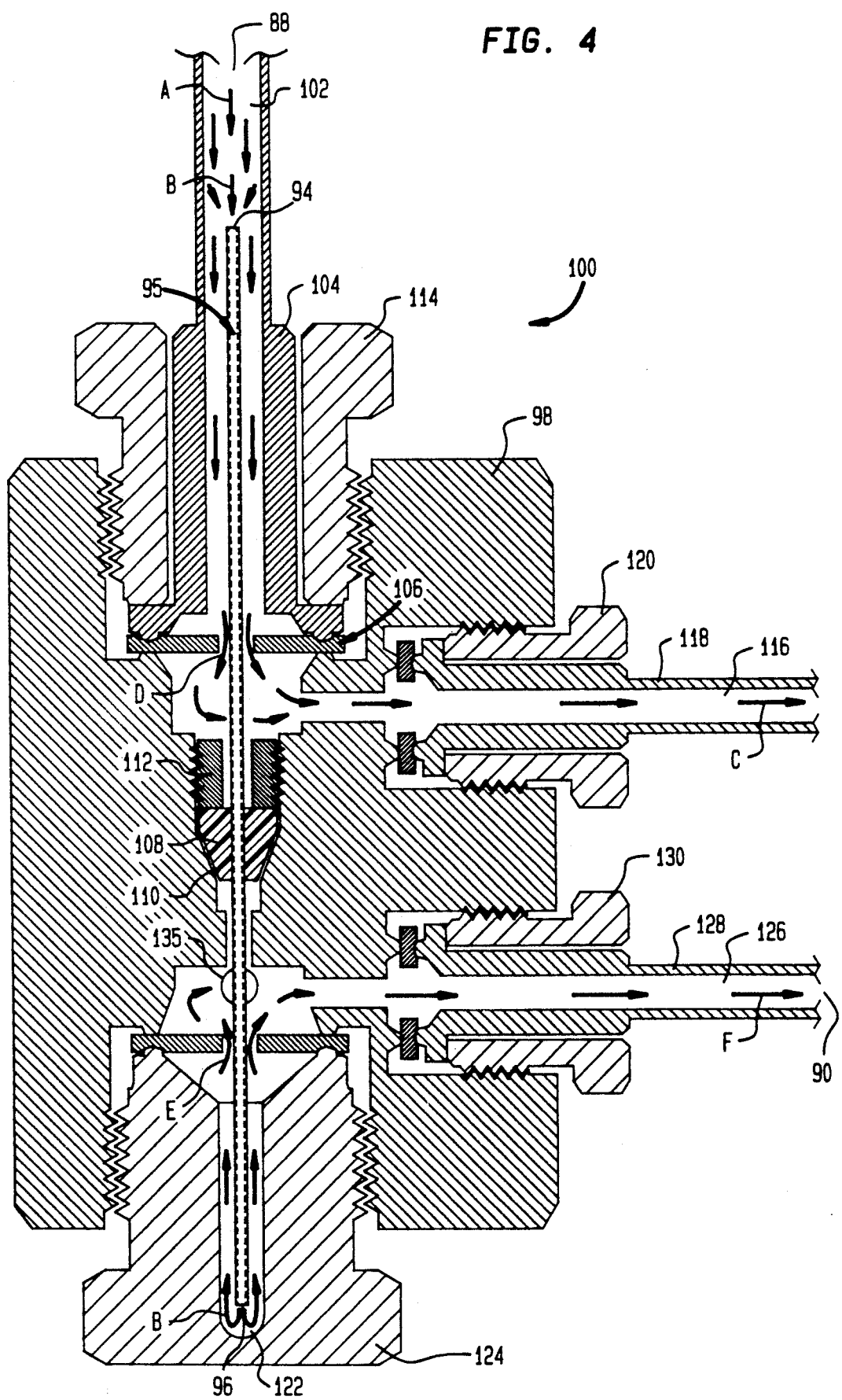
FIG. 4 shows the counterflow arrangement applied to an electrolytic cell with an epoxy-less configuration incorporating a soft ferrule, glass-metal seal and welded ceramic feedthroughs.

As shown in FIG. 4, the counterflow configuration of the present invention can be applied to an epoxy-less electrolytic cell incorporating a soft ferrule, glass-metal seal combined with welded ceramic feedthroughs. Details about the soft ferrule, glass-metal seal and the welded ceramic feedthroughs are described in the co-pending United States application entitled "Epoxy-Less Low-Level Moisture Measurement System and Method" mentioned above.

In FIG. 4, the gas to be sampled, designated by arrow A, enters channel 102 formed by tubing 104. Tubing 104 is held in housing 98 by a connection, which may be manufactured under the VCR® trademark by the Cajon Company, using nut 114. As gas A passes down channel 102, it encounters entrance 94 of detection unit 95. At entrance 94, gas A separates into sample gas B, which passes into unit 95 and is analyzed, and gas D. Rather than enter unit 95, gas D passes between unit 95 and tubing 104 and forms a counterflow to protect entrance 94 from contamination.

A VCR® gasket 106 seals tubing 104 against housing 98. The central opening of gasket 106 and that of the gasket used to connect the plug 124 (discussed below) have a diameter which is minimized to create a locally high speed flow through the narrow passages of the gaskets. Such a flow increases the effectiveness of the counterflow. The diameters of the gaskets are still sufficiently large, however, to pass detection unit 95 and to allow easy installation.

Gas D passes between unit 95 and gasket 106 and, blocked by compressible seal 108, exits cell 100 as bypass gas C through a channel 116 formed by tubing 118. Tubing 118 is held in housing 98 by a VCR® connection using nut 120. Any moisture which might leak from seal 108 must travel upward against the stream of gas D to reach entrance 94 and contaminate sample gas B. The previously discussed effects of a flow provided by gas D make such counterflow difficult, if not impossible: thus, contamination of sample gas B is significantly reduced.

Similarly, a counterflow geometry is provided near exit 96 to prevent contamination of sample gas B. A cavity 122 formed in the VCR® plug 124 redirects sample gas B as it leaves exit 96 and creates a flow designated by arrow E. That flow prevents contamination from entering exit 96. The diameter of the central opening of the gasket used to connect plug 124 is sufficiently large both to pass detection unit 95 and to provide enough space for the two electrode wires (not shown in FIG. 4) stretched alongside the outside of detection unit 95 to pass without contacting the gasket. Details about the stretched electrode wires are provided in the discussion of FIG. 5.

Counterflow E subsequently leaves cell 100 as exit gas F through a channel 126 formed by tubing 128. Tubing 128 is held in housing 98 by a VCR® connection using nut 130. Any moisture which might leak from seal 108 must travel downward against the flow of gas E to reach exit 96 and contaminate sample gas B. The presence of gas flow E makes such counterflow difficult, if not impossible; thus, contamination of sample gas B is significantly reduced.

Seal 108 is preferably a conical-shaped ferrule formed from a soft, compressible material. The shape of seal 108 permits it to engage a frustroconical taper 110 in housing 98. A threaded lock screw 112 having an extra fine thread engages mating threads on housing 98. As screw 112 is screwed into housing 98 it contacts seal 108, exerting a downward force on seal 108 and pressing seal 108 into sealing abutment against taper 110. A horizontal force component is thereby generated, forcing seal 108, which is positioned near the center of detection unit 95 and surrounds unit 95, to fix unit 95 concentrically within housing 98. Pressed against unit 95 and taper 110, seal 108 also prevents leakage of gas between inlet 88 and outlet 90 of cell 100. Such leakage would otherwise bypass the sample flow through unit 95 of cell 100 and cause an erroneous calculation of the moisture concentration in that sample flow.

In order to usefully apply the forces generated by the combination of screw 112 and taper 110, seal 108 must be compressible. Seal 108 must be soft so that it secures detection unit 95, which is usually glass, safely. Suitable materials for seal 108, therefore, include plastics such as Teflon®. It would be ideal to eliminate all plastics from the high purity gas system. The combination of plastic seal 108, screw 112, and taper 110 with the counterflow geometry approaches, in a practical system, that ideal.

Figure 5:
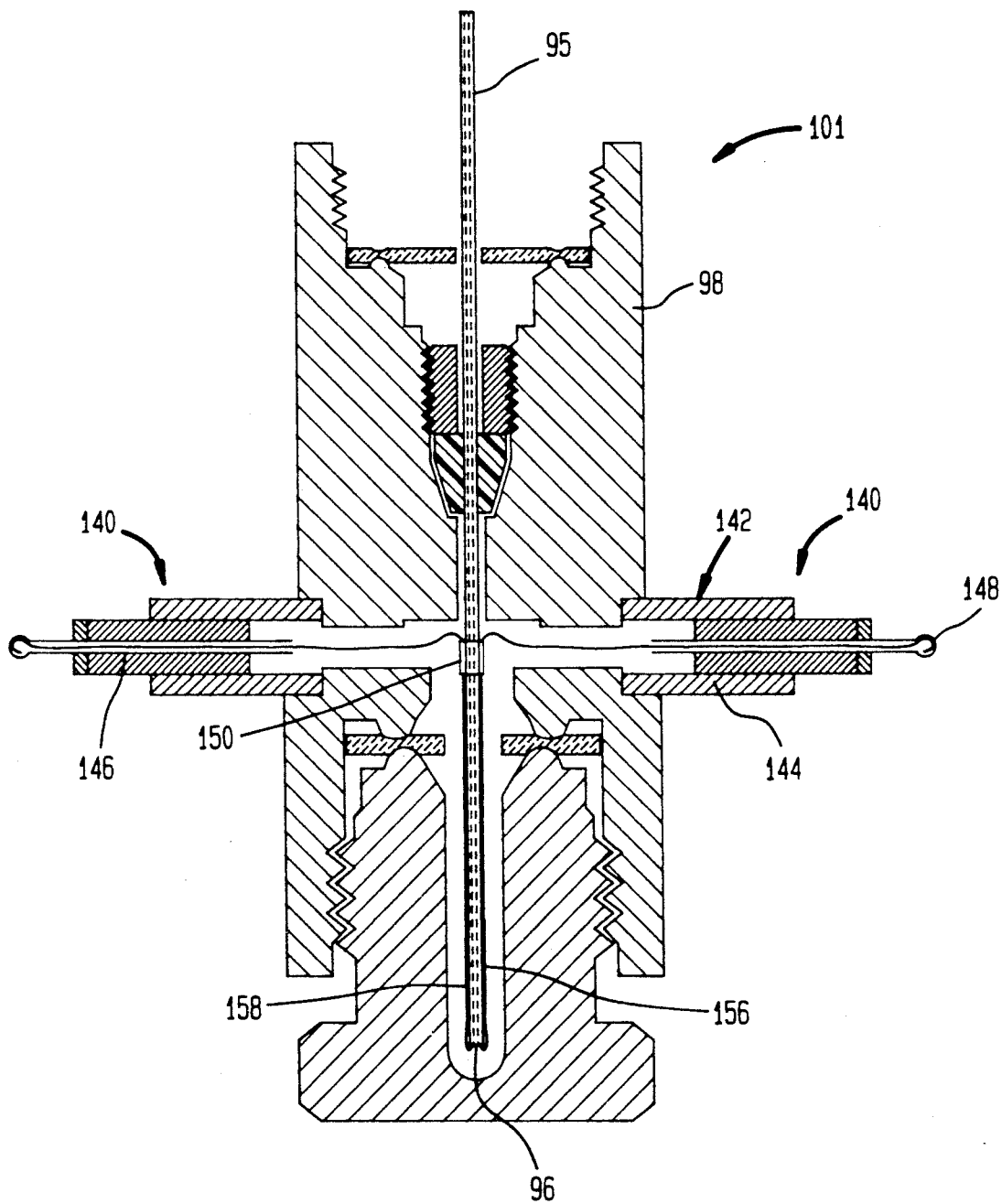
FIG. 5 is a cross-section of the cell shown in FIG. 4 highlighting the weldable or solderable, electrical, leak tight, ceramic feedthrough for the electrodes.

In order to provide an electrical insulator, for carrying the electrode wires to further electrical connections (not shown) outside the cell 100, and a leak-proof barrier where the electrode leads pass through cell 100, a pair of electrical insulator assemblies 140 are sealingly fixed to housing 98 (see FIG. 5). Insulator assemblies 140 may be horizontally disposed in housing 98 at an axial position denoted by the circle 135 in FIG. 4.

FIG. 5 is a cross-section of the cell shown in FIG. 4 highlighting the electrical insulator assemblies 140. Assemblies 140 provide leak-tight, electrical insulators and weldable ceramic feedthroughs. FIG. 5 shows electrical insulator assemblies 140 in detail. In contrast, the insulator assemblies 140 are disposed perpendicular to the plane of FIG. 4 and, hence, are not shown in detail in that Figure.

In one embodiment of electrical insulator assemblies 140, weld lips 142 are provided to be connected to housing 98. Connections 142 sealingly hold insulating blocks 144, typically made of ceramic. Disposed through the center of insulating blocks 144 are electrical terminals 146, in this case shaped as hollow, metal tubes. Terminals 146 extend from inside housing 98 to outside connections 142 on housing 98. Inside terminals 146, electrode wires 156, 158 are carried from within housing 98 to outside housing 98. Solder 148 closes off, in a leak-tight manner, the ends of terminals 146 and electrically connects electrode wires 156, 158 to those terminals. Thus, electrode wires 156, 158 can be further electrically connected to external electrical equipment.

Wires 156, 158 helically cover the interior of unit 95 until they reach exit 96 of unit 95. There, once outside unit 95, wires 156, 158 proceed to enter, one each, terminals 146. As shown in FIG. 5, wires 156, 158 proceed along the outside of unit 95 to reach terminals 146. Small, cylindrical pieces of shrink tube 150 retain wires 156, 158 and prevent contact between the wires and the gasket.

Although the system of the present invention for measurement of fluid moisture content is effective for low level water analyses, on the order of five parts per billion by volume, it will be understood that the invention is also applicable to the measurement of higher water concentrations. It should also be understood that, although the details of the present invention are discussed above in relation to an electrolytic cell, the counterflow configuration can be applied to other types of moisture-measurement devices and methods. Even more generally, the counterflow configuration of the present invention can be applied both to analyzers which measure moisture or other impurities in gases and contain moisture-sensitive or, as just discussed, other impurity-sensitive components and to methods using such apparatuses.

Finally, it will be understood that the foregoing embodiments of the invention are illustrative only and that various changes can be made in the form, details, spatial arrangements, materials, and proportions of the various components of such embodiments without departing from the spirit and scope of the invention as defined by the appended claims.

What is claimed is:

1. A counterflow device for an analyzer engaging a gas stream and having a sensor including an entrance, an exit, and means for measuring a component of said gas stream, said device comprising:
   a housing having an inlet for said gas stream and an outlet for said gas stream;
   means fixing said sensor within said housing, said housing and said sensor defining a cavity therebetween;
   at least one element disposed in said cavity between said entrance and said exit of said sensor which emits an impurity; and
   means for directing a portion of said gas stream into said cavity as a counterflow toward said at least one impurity-emitting element and out said outlet, said counterflow flowing against movement of impurities from said element toward at least one of said entrance and said exit of said sensor.

2. A device as claimed in claim 1 wherein said impurity is moisture and said entrance and said exit of said sensor are located a distance from said element sufficient to isolate said element from said entrance and said exit, thereby minimizing migration of the impurity from said element to said entrance and said exit of said sensor.

3. A device as claimed in claim 2 wherein said sensor is a hygrometer and said measured component of said gas stream is moisture.

4. A device as claimed in claim 3 wherein:
   the remainder of said gas stream which does not form said counterflow forms a sample gas flow which enters said entrance of said sensor and exits said exit of said sensor;
   said at least one moisture-emitting element is downstream of said entrance of said sensor in said counterflow; and
   said counterflow exits said outlet of said analyzer without entering said sensor.

5. A device as claimed in claim 3 wherein:
   at least a portion of said gas stream enters said entrance of said sensor and forms a sample gas flow;
   said sample gas flow forms said counterflow upon exiting said exit of said sensor;
   said at least one moisture-emitting element is downstream of said exit of said sensor in said counterflow; and
   said counterflow exits said outlet of said analyzer without further contacting said measuring means of said sensor.

6. A device as claimed in claim 4 further comprising a soft material partially surrounding said sensor for securing said sensor in said housing, said soft material constituting said at least one element disposed between said entrance and said exit of said sensor which emits an impurity.

7. A device as claimed in claim 5 further comprising a soft material partially surrounding said sensor for securing said sensor in said housing, said soft material constituting said at least one element disposed between said entrance and said exit of said sensor which emits an impurity.

8. A device as claimed in claim 3 wherein the remainder of said gas stream which does not form said counterflow forms a sample gas flow and said sensor includes:
   a tubular conduit having an entrance and an exit for said sample gas flow;
   at least one pair of electrically isolated wires helically disposed in parallel on the interior wall of said conduit, said wires covering approximately half of the surface area of the interior wall exposed to said sample gas flow between said entrance and said exit, and
   a water absorbent coating on said wires.

9. A device as claimed in claim 8 further comprising a soft material partially surrounding said sensor for securing said sensor in said housing, said soft material constituting said at least one element disposed between said entrance and said exit of said sensor which emits an impurity.

10. A device as claimed in claim 9 wherein said soft material forms a compression seal between said conduit of said sensor and said housing.

11. A device as claimed in claim 9 further comprising:
    means for conducting electrical signals to and from said sensor.

12. A device as claimed in claim 11 wherein said soft material is a packing material which embeds said electrodes.

13. A device as claimed in claim 9 further comprising:
    a first outlet channel;
    an inlet channel adapted to direct said sample gas flow into said entrance of said conduit of said sensor, said exit of said conduit of said sensor being adapted to direct said sample gas flow at said soft material when said sample gas flow exits said sensor, said portion of said gas stream forming said counterflow bypassing said sensor and blanketing said soft material before exiting said analyzer via said first outlet channel; and
    a second outlet channel being an outlet for said sample gas flow exiting said sensor.

14. A device as claimed in claim 9 wherein said directing means includes an inlet sleeve between said conduit and said housing for directing said counterflow onto the surface of said soft material, said sleeve redirecting said counterflow between the exterior of said sleeve and said housing towards said outlet.

15. A device as claimed in claim 9 further comprising a dam surrounding said exit of said conduit of said sensor for redirecting said sample gas flow exiting said sensor toward said soft material before said sample gas flow reaches said outlet.

16. A device as claimed in claim 9 wherein said conduit is glass, said housing is electroplated stainless steel, and said soft material is epoxy resin.

* * * * *